United States Patent [19]

Cheng

[11] 3,936,385

[45] Feb. 3, 1976

[54] DENTURE CLEANSER

[75] Inventor: Shu-Sing Cheng, Hanover Park, Ill.

[73] Assignee: Colgate-Palmolive Company, New York, N.Y.

[22] Filed: Aug. 9, 1973

[21] Appl. No.: 387,075

[52] U.S. Cl. .................. 252/99; 252/103; 252/157; 252/187 H; 252/350; 424/44; 424/53; 424/130; 424/149

[51] Int. Cl.² ............................................ C11D 7/54

[58] Field of Search ............ 252/99, 103, 157, 350, 252/187 R, 187 C, 187 H, 186; 424/44, 53, 56, 57, 130, 149

[56] References Cited
UNITED STATES PATENTS

| | | | |
|---|---|---|---|
| 3,337,466 | 8/1967 | Puetzer et al. | 252/99 |
| 3,355,392 | 11/1967 | Cantor et al. | 252/99 |
| 3,640,879 | 2/1972 | Fitzgerald | 252/103 |
| 3,671,629 | 6/1972 | Levy et al. | 424/153 |
| 3,793,211 | 2/1974 | Kohlhepp et al. | 252/99 |
| 3,821,117 | 6/1974 | Breece et al. | 252/99 |

*Primary Examiner*—Thomas J. Herbert, Jr.
*Assistant Examiner*—Bruce H. Hess
*Attorney, Agent, or Firm*—Herbert S. Sylvester; Murray M. Grill; Norman Blumenkopf

[57] ABSTRACT

Effervescent denture cleanser having excellent plaque-removing properties. It comprises a source of free chlorine, such as a dichloroisocyanurate, and a peroxygen compound effervescently reactive therewith in water, so as to give a denture soaking solution containing at least 100 ppm active chlorine and having a pH of at least about 9, preferably at least 10, and more preferably about 10.6 to 11.5.

21 Claims, No Drawings

DENTURE CLEANSER

This invention relates to effervescent denture cleansers, particularly suitable for the removal of the plaque which forms on dentures when they are worn in the mouth. In using the denture cleansers of this invention the denture may be simply soaked for a relatively short period of time in water in which the denture cleanser, in tablet or powder form, has been placed. No mechanical stirring is required; the effervescence of the composition is sufficient to effect sufficient agitation and rapid dissolution of the solid composition in the water.

Effervescent denture cleansers have long been known in the art. Most of those presently on the market derive their cleansing efficiency mainly from peroxy compounds which provide active oxygen. While the active oxygen does show a good bleaching action, e.g. on certain dyes, it has relatively poor plaque-removing properties. Various peroxygen type denture cleansers are described in U.S. Pat. Nos. 2,498,343; 2,498,344; 2,931,776; and 3,243,377.

Another type of denture cleanser on the market uses strong acidic solutions. This too has poor plaque removing properties.

Still another type of denture cleanser, described in U.S. Pat. No. 3,113,111, derives its cleansing efficacy mainly from an active chlorine source and has good plaque-removing properties. It is not, however, effervescent and has a relatively slow rate of dissolution unless stirred mechanically.

Effervescent denture cleansers made with sodium perborate monohydrate and sodium dichloroisocyanurate have been suggested (as in the bulletins of the FMC Corp., which is a supplier of both these ingredients). These cleansers contain, for instance, 9 to 12% of the perborate and 2–4% of the diisocyanurate together with certain alkaline ingredients (to give a pH of about 7.3–8.1) and are used in amount to provide about 200 ppm active oxygen and substantially no hypochlorite chlorine. Like other conventional peroxygen-type denture cleansers they have poor plaque-removing properties.

In accordance with one aspect of this invention there is provided a solid denture cleanser composition which, on addition to water, effervesces and dissolves quickly giving a solution which is highly effective for the removal of plaque from dentures soaked therein for relatively short periods of time. The solid composition, in dry powder or tablet form, is substantially stable on storage.

One form of denture cleanser in accordance with the invention is an alkaline mixture containing a chlorine compound which liberates hypochlorite chlorine on contact with water and a peroxygen compound which reacts with a component of said mixture in water to liberate oxygen, the proportions of the ingredients being such that, when the composition is incorporated into the water in which the denture is to be soaked, the concentration of active chlorine in the water is at least about 100 ppm (preferably above about 400 ppm such as in the range of 500 to 1500 ppm) and the pH of the water is at least about 9, preferably at least 10, more preferably above 10.5; a particularly suitable range is about 10.6–11.5. The concentration of active chlorine in the water can be readily measured by conventional chemical analysis such as by addition of potassium iodide to the solution and titration for the amount of iodine (the latter being liberated from the KI by the action of the active chlorine); this analysis can be made conveniently just after bubbling substantially ceases.

The alkalinity of the composition may be provided by the inclusion therein of a suitable amount of an alkaline material such as an anhydrous alkaline alkali metal salt.

A particularly suitable chlorine compound which liberates hypochlorite chlorine on contact with water is a heterocyclic N-chloro imide, e.g., a chloroisocyanurate such as sodium dichloroisocyanurate, potassium dichloroisocyanurate, or trichloroisocyanuric acid, or a complex salt of two or more of these materials, e.g. [(mono-trichloro)-tetra-(monopotassium-dichloro)] penta-isocyanurate. Other N-chloro imides which may be used are sodium p-toluenesulfonohloramide, N,N-dichloro-p-toluenesulfonamide, sodium benzenesulfonchloramide, N,N-dichlorobenzenesulfonamide, N-chlorosuccinimide. Still other compounds which liberate hypochlorite chlorine on contact with water are other imides such as N-chloro malonimide, N-chloro phthalimide and N-chloro naphthalimide, the hydantoins such as 1,3-dichloro-5,5-dimethyl hydantoin; N-monochloro-C,C-dimethylhydantoin; methylene-bis (N-chloro-C,C-dimethylhydantoin; 1,3-dichloro-5-methyl-5-isobutyl-hydantoin; 1,3-dichloro-5-methyl-5-ethylhydantoin; 1,3-dichloro-5,5-diisobutylhydantoin; 1,3-dichloro-5-methyl-5-n-amylhydantoin, and the like. Other hypochlorine-liberating agents are trichloromelamine and dry, particulate, water-soluble anhydrous inorganic salts such as lithium hypochlorite and calcium hypochlorite. It will be understood that two or more of the chlorine compounds may be employed in admixture.

The peroxygen compound is one which yields active oxygen on admixture with water. It may, for example, be a peroxyhydrate or hydrogen peroxide addition compound as described, for instance in Kirk-Othmer Encyclopedia of Chemical Technology first edition Vol. 10, published 1953, pages 49ff, which may comprise a borate, carbonate or phosphate. Particularly suitable compounds of this type are sodium perborate monohydrate and sodium carbonate peroxyhydrate (such as $Na_2CO_3 \cdot 1\frac{1}{2} H_2O_2$). Other very suitable peroxygen compounds are monopersulfates such as potassium monopersulfate, $KHSO_5$. Other peroxygen compounds which may be present are, for instance, succinic acid peroxide, sodium peroxide and calcium peroxide.

Particularly suitable materials to provide the alkalinity of the composition are trisodium phosphate (a compound which in dilute aqueous solution, e.g. at 0.1–1% concentration, has a pH of 11.5–11.9) or sodium carbonate (whose dilute aqueous solutions have a pH which is generally above 11). Another highly alkaline salt is sodium metasilicate. Less alkaline salts, such as $NaHCO_3$, $Na_2HPO_4$, pentasodium tripolyphosphate and tetrasodium pyrophosphate may also be present in admixture with the more alkaline compounds. The alkalinity, or a portion thereof, may also be provided by suitable hydroxides or peroxides, e.g. NaOH or sodium peroxide.

The ingredients of the composition are preferably of sufficiently low water content that the composition is stable on storage, e.g. it retains over 90% of its active oxygen and chlorine contents, and preferably over 95% thereof, on storage for 30 days at room temperature (e.g. 25°C) in a sealed container; preferred compositions retain over 95% of said contents for at least 180 days under these conditions. To this end the alkalinity-imparting material employed, and the other components, are preferably substantially anhydrous.

The denture cleansers of the invention are typically intended for use in concentrations of about 2 to 5 grams (preferably about 3 to 4 grams) per 120 ml. of water.

In the most preferred forms of the invention, the metallic cations present in the compositions are substantially entire sodium and/or potassium. These may be replaced, at least in part, by other appropriate cations (such as Mg, Li, Ca, Sr, Ba), it being preferred that compounds which are water-soluble be employed.

In one form of the invention the peroxygen compound is one which reacts with the chlorine compound and is decomposed by that reaction to liberate oxygen gas, causing effervescence. For example the reaction of sodium dichloroisocyanurate and a hydrogen peroxide addition compound such as sodium perborate monohydrate in the presence of trisodium phosphate may be represented by the following equation:

fate (such as potassium monopersulfate) and the chlorine compound is placed in water. When, however, the trisodium phosphate is present in admixture with this blend vigorous effervescence occurs. This is believed to be due to a reaction between the trisodium phosphate and the monopersulfate yielding oxygen gas; it is within the broader scope of this invention to employ this reaction for forming other effervescent denture cleansers, such as cleansers having no active chlorine. Vigorous effervescence also occurs when a carbonate such as sodium carbonate is present in admixture with such a blend (of monopersulfate and chlorine compound); in that case it is believed that the gas is, at least in part, carbon dioxide. In any case, in the preferred cleansers the effervescence is substantially complete in less than 10 minutes, such as about one to five minutes.

The chlorine compound is preferably present in an amount having an active chlorine content of over 0.2% (e.g. about 1–10%, more preferably about 2 to 8%) of the total composition in addition to any amount of active chlorine that is consumed in the effervescent

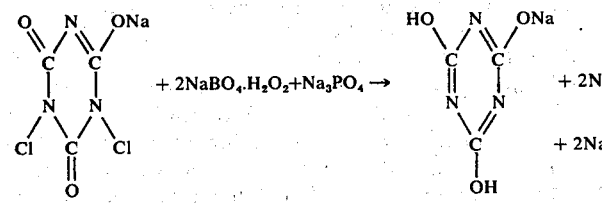 

In that equation the two molecules of sodium perborate are equivalent to two atoms of active oxygen and the one molecule of sodium dichloroisocyanurate is equivalent to two atoms of active chlorine, so that there is a 1:1 ratio of active chlorine to active oxygen in the components. It is preferred that this ratio be greater than 1:1 in the components, such as at least 1.1:1. For best results, in terms of vigorous effervescence providing rapid dissolution and rapid homogeneous mixing with high plaque removal effectiveness, it is preferred that this ratio be about 2:1 to 3:1 or more; that is, the preferred amounts provide at least about two atoms (and more preferably about 2.2 atoms) of hypochlorite chlorine, from the chlorine compound, for each atom of active oxygen.

The preferred proportions are such as to provide sufficient effervescence that the composition (in the form supplied, e.g. as a tablet or as granules) dissolves substantially completely in water (e.g. in 120 ml of water at 49°C, using about 3–4 grams of composition) in well below 10 minutes, and generally less than 5 minutes, e.g. about 2 to 4 minutes, without mechanical stirring. It should be noted that, in the absence of the effervescent effect, certain water-soluble materials present in the dry composition do not go into solution quickly; for instance, anhydrous trisodium phosphate powder when brought into contact with water tends to hydrate and form clumps or lumps which are slow to dissolve. The peroxygen compound is preferably present in an amount having an active oxygen content of more than 0.1% of the total composition, such as in the range of about 0.2 to 2% (e.g. about 0.4 to 1.3%) active oxygen.

As indicated above, effervescence can be produced by the reaction of the chlorine compound and a hydrogen peroxide addition product. No effervescing reaction takes place when a simple blend of a monopersulreaction.

In one preferred form of the invention the composition contains a plurality of oxidizable dyes which are oxidized at different rates to serve as a time lapse indicator to enable the user to know how long the denture has been soaking and thus to know when to remove it from the soak solution if longer term soaking is not desired. One dye, whose color predominates initially, is of a type which is more rapidly bleached than the other. For instance, the composition may contain a blue dye (such as FD&C Green No. 3) mixed with a smaller amount of a more oxidation-resistant red dye (such as FD&C Red No. 3). The solution is initially blue when the tablet is dropped into warm water (e.g. at 120°F, 49°C); after 7 minutes the color changes to purple, because the blue dye has been so bleached that the effective concentrations of blue and red are now similar, giving a purple appearance; after 3 more minutes the blue has been practically all bleached out and the solution is thus pink in color, owing to the continued presence of the red dye; after about 35 more minutes (i.e. a total of about 45) the solution has become colorless. The use of a plurality of dyes in this manner constitutes another feature of this invention and, in its broader aspects, this feature may be used in other denture cleanser compositions, such as known non-effervescent compositions providing active chlorine or even known compositions providing other bleaching species such as active oxygen. Usually the proportion of dye or other coloring agent is less than 1%, preferably less than ½% of the composition. The time periods at which color changes occur can be controlled by the proportions of the dyes; e.g. an increase in the amount of the readily bleachable blue dye in the composition causes the color change to occur after a longer soaking time. Preferably the proportions are such that a color change occurs within several minutes, but less than one hour, from the time that the cleanser and water are brought together.

The denture cleanser may also contain a surfactant in amount sufficient to promote foaming during effervescence (e.g. about 0.01 to 1%, such as about 0.1%). The surfactant may be of any of the well known types (e.g. anionic, nonionic, cationic, amphoteric); thus it may be an anionic surfactant having a long hydrophobic alkyl chain (e.g. of about 8–20 carbon atoms) attached to a hydrophilic ionic portion such as sulfate or sulfonate radical (e.g., sodium lauryl sulfate). See U.S. Pat. No. 2,498,344 of Feb. 21, 1950, column 6, for a discussion of the use of wetting agents in effervescing denture cleaners.

The composition may be conveniently formed into tablets, by conventional techniques, as by mixing the powders together and subjecting them to tabletting pressure. The compositions may contain conventional tabletting aids, such as binders and/or lubricants and/or disintegrating aids for this purpose. Examples of these materials, which are preferably substantially inert under the conditions to which the compositions are subjected, are well known in the art. Thus, one may employ the materials listed in "Remington's Practice of Pharmacy" by Martin and Cook, 12th edition (published 1961 by Mack Publishing Company, Easton, Pa., and the tabletting techniques described there, as at p.443–454. Among these materials are, for instance, glucose, gum acacia, gelatin, sucrose, starches, talc, magnesium stearate, polyethylene glycol of various average molecular weights (e.g. 600 or 4000), etc. The tabletting aids are generally present in total amount which is less than half (usually well below 40%) of the total weight of the composition. The size of the tablet may vary, generally its volume is in the range of about 1 to 5 cc, such as about 3 cc.

The composition may also be in the form of a powder, e.g. small granules having particle sizes within the range such as to pass through a 10 or 20 mesh sieve and be retained on, say a 40 mesh sieve (all sieve sizes herein being U.S. Standard). It is preferable that most of the granules have substantially the same overall composition, so that the individual granules will be effervescent. To this end the granules may be produced by thoroughly mixing finely powdered ingredients, forming the uniform mixture into tablets, then breaking up the tablets mechanically, and screening to obtain the desired sizes of granules. Other known techniques for forming granules of substantially uniform composition may be employed.

The following Examples are given to illustrate this invention further. Unless otherwise stated, all proportions in this application are by weight.

EXAMPLES 1–5

The following are formulations for making suitable effervescent denture cleaning tablets.

|  | 1 | 2 | 3 | 4 | 5 |
|---|---|---|---|---|---|
| Fragrance | 1.0000% | 1.500% | 1.0000% | 1.0000% | 1.0000 |
| Amaranth (FD&C Red No. 2) | — | — | — | — | 0.0200 |
| Erythrosin (FD&C Red No. 3) | 0.0025 | 0.0025 | 0.0025 | 0.0025 | — |
| Fast Green (FD&C Green No. 3) | 0.0200 | 0.0200 | 0.0200 | 0.0200 | — |
| Violet 5NB (FD&C Violet No. 1) | — | — | — | — | 0.0400 |
| Sodium lauryl sulfate | 0.1000 | 0.1000 | 0.1000 | 0.1000 | 0.1000 |
| Polyox WSR N-10 | 1.0000 | 2.0000 | 10.0000 | 10.0000 | 10.0000 |
| Sodium perborate monohydrate | 7.0000 | 7.0000 | 7.0000 | — | — |
| Sodium dichloroisocyanurate | 17.0000 | 17.0000 | 17.0000 | 8.0000 | — |
| Potassium dichloroisocyanurate | — | — | — | — | 9.0000 |
| Hydrolyzed Cereal Solids | — | — | 15.0000 | 15.0000 | 15.0000 |
| Potassium monopersulfate | — | — | — | 16.0000 | 16.0000 |
| Sodium peroxide | — | — | — | — | 1.0000 |
| Anhydrous sodium carbonate | — | — | — | — | 47.8795 |
| Anhydrous trisodium phosphate | 73.8775 | 72.3775 | 49.8775 | 49.8775 | — |

The tablets are made by intimately mixing fine powders of the materials (particle size such that 95% or more of each powder passes through a 100 mesh sieve) and pressing the mixture in a rotary tabletting press, using maximum pressure of 10,000 lbs/in$^2$ to a hardness of about 10 to 12 Strong-Cobb units. The mass of each tablet is about 3.6 grams and its volume is about 3cc (e.g. a round flat tablet 1 inch in diameter and about three-eighths inch in thickness). The Polyox WSR N-10 is a water-soluble solid ethylene oxide polymer of molecular weight about 100,000 which acts as a binder, lubricant and disintegrant; the hydrolyzed cereal solids, which serves as a disintegrant, is a water-soluble material sold as "1918 Mor-Rex" by CPC International Inc. containing polysaccharides (about 4% di-, 5% tri, 4% tetra-, 4% penta-, 82% hexa- and above) and 1% glucose. The dry compositions contain small amounts of water; thus the manufacturer's specifications for the hydrolyzed cereal solids, as sold, indicate that it contains up to about 5% water; commercial anhydrous trisodium phosphate has up to 1½% water; commercial anhydrous sodium carbonate has up to 1% water; the manufacturer's specifications for the Polyox material indicate it has up to 5% water.

When the tablet of Example 3 is placed in 120 ml water at 49°C and the 3.6 g tablet is permitted to effervesce completely in the water the pH of the resulting solution is 11.35; the pH does not change materially during soaking of the denture therein. Measurements of active chlorine content of the solution (using the tablet of Example 3) are as follows: the time period after the tablet is dropped into the water being indicated in parentheses: 720 ppm (14 minutes), 711 (20 minutes), 693 (0.8 hour), 677 (1.5 hours), 677 (2 hours), 391 (18 hours), 320 ppm (24 hours) 8.8 ppm (141 hours); the active chlorine content at the outset (e.g. after the 14 minute period) is in the neighborhood of 80% of the active chlorine content calculated from the proportions of diisocyanurate and sodium perborate, taking into account the equation, given above, for the reaction of these components, thus indicating that some of the active chlorine is consumed in reactions with other components of the tablet.

It will be noted that Example 5 contains also sodium peroxide to provide an active oxygen source of greater alkalinity in view of the loss of sodium carbonate by reaction with the potassium monopersulfate. Even with this addition the pH of the solution is only about 10.25 and the product is not preferred.

EXAMPLES 6–10

The following are formulations for making suitable effervescent denture cleansers, in granular form.

|  | 6 | 7 | 8 | 9 | 10 |
|---|---|---|---|---|---|
| Fragrance | 1.0000% | 1.0000% | 1.0000% | 1.0000% | 1.0000% |
| Erythrosin (FD&C Red No. 3) | 0.0025 | — | 0.0025 | — | — |
| Fast Green (FD&C Green No. 3) | 0.0200 | — | — | — | 0.0200 |
| Amaranth (FD&C Red No. 2) | — | 0.0040 | — | — | — |
| Malachite Green | — | 0.1000 | — | 0.1000 | — |
| Violet 5NB(FD&C Violet No. 1) | — | — | 0.4000 | 0.0400 | — |
| Polyox WSR N-10 | 5.0000 | 5.0000 | 5.0000 | 5.0000 | 5.0000 |
| Sodium perborate monohydrate | 4.9000 | 3.0000 | — | — | 4.0000 |
| Sodium dichloroisocyanurate | 11.7000 | 8.0000 | — | — | 4.0000 |
| Potassium dichloroisocyanurate | — | — | 9.0000 | 9.0000 | — |
| Hydrolyzed cereal solids | 10.0000 | 10.0000 | 10.0000 | 10.0000 | 10.0000 |
| Potassium monopersulfate | — | 10.0000 | 10.0000 | 10.0000 | — |
| Anhydrous sodium carbonate | — | — | 64.5975 | — | — |
| Anhydrous trisodium phosphate | 67.3775 | 62.8960 | — | 64.8600 | 69.9800 |
| Trichloroisocyanuric Acid | — | — | — | — | 6.0000 |

EXAMPLE 11

A tablet is prepared as, in Examples 1–5, from a mixture of powders of the following ingredients: 3% sodium carbonate peroxyhydrate (14.19% active oxygen content); 14% sodium dichloroisocyanurate; 15% of the hydrolyzed cereal solids of Examples 3–10; 10% of the ethylene oxide polymer of Examples 1–10; 0.1% sodium lauryl sulfate; 1% fragrance; 0.02% FD&C Green No. 3; 56.88% anhydrous trisodium phosphate. A solution formed from the tablet, as in Example 1, shows an active chlorine content (measured about 20 minutes after the tablet is added to the water) of about 1270 ppm.

EXAMPLE 12

Example 11 is repeated but the content of sodium carbonate peroxyhydrate is increased to 4.5% and the trisodium phosphate content is correspondingly reduced to 55.38%. The active chlorine content of the solution measured as in Example 11 is about 850 ppm.

EXAMPLE 13

Example 11 is repeated but the content of sodium carbonate peroxyhydrate is increased to 6% and the trisodium phosphate content is correspondingly reduced to 53.88%. The active chlorine content of the solution measured as in Example 11 is about 640 ppm.

The pH values of the solutions formed from the tablets of Examples 11 to 13 (using a 3.6g tablet in 120 ml of water) are in the range of about 11.2 to 11.3. For the solutions formed from the compositions of Examples 6 and 8 (using the same concentrations) the pH values are 11.5 and 10.45.

EXAMPLE 14

The denture cleanser of this Example is a mixture of dry fine powders, comprising 7% powdered sodium perborate monohydrate, 17% powdered sodium dichloroisocyanurate and 76% powdered anhydrous trisodium phosphate. In use, 2 grams of the mixture is placed in a vessel and 60 ml of warm tap water (at 49°C) is added without stirring. Vigorous effervescence occurs. The resulting solution, having a pH of about 11.4 to 11.5 and containing in the neighborhood of 1560 ppm of active chlorine, is very suitable for cleaning dentures by soaking.

EXAMPLE 15

The denture cleanser of this Example is a mixture of dry fine powders, comprising 7.7% powdered sodium perborate monohydrate, 18.7% powdered sodium dichloroisocyanurate, 65.2% powdered $Na_2HPO_4$ and 8.4% powdered anhydrous trisodium phosphate. In use, 4.5 grams of the mixture is placed in a vessel and 120 ml of warm tap water (at 43°C) is added without stirring. Vigorous effervescence occurs. The resulting solution, having a pH of about 9.0, is effective for cleaning dentures by soaking. Much better results are obtained when the relative proportions of $Na_2HPO_4$ and $Na_3PO_4$ are varied (to change the weight ratio of these components to 0.87:1) so as to give a pH of 10.6.

On standing, the solutions formed from the compositions of Examples 1–4 and 6 (which contain Erythrosin and Fast Green) show the color changes described earlier. The solutions of Example 5 and 8 change from violet to purple to pink; the solution of Example 7 changes from green to gray to pink.

The denture cleansers of this invention form soaking solutions which are safe and non-toxic and can be removed readily from the denture, by simple rinsing with running water.

The content of active chlorine can be determined by conventional analysis as follows: Cool the solution to room temperature, then add (to 120 ml of the solution) one gram of potassium iodide; this causes the solution to turn brown owing to the liberation of iodine by the action of the active chlorine. Then titrate with 0.1 N aqueous solution of sodium thiosulfate until the brown color just disappears, then acidify with 3 ml of 50% aqueous solution of $H_2SO_4$ (which causes the solution to turn brown again), continue titrating with the sodium thiosulfate until the solution becomes light yellow, then add starch which causes the solution to turn blue (owing to the reaction of the starch with the remaining iodine) and then titrate with the sodium thiosulfate until the blue color disappears. The calculation of the ppm of active chlorine based on the volume of sodium thiosulfate solution used for titration is conventional.

The plaque removal and bleaching actions of denture cleansers may be measured in the following manner: A denture worn by a person for 16–24 hours without cleaning is rinsed in water to remove saliva and the loose food particles. It is then stained in a 1% aqueous solution of a red dye (erythrosin) for 2 minutes to disclose the location and amount of oral deposit (plaque) on the denture. The plaque is stained in red color. The deeper the red color of the denture, the heavier the plaque accumulation. The stained denture is passed through seven rinses of water to remove the excessive dye not adhering to the plaque. The denture may then be photographed (e.g. with color slide transparency) for the purpose of recording its appearance. For a bleaching efficacy test, the stained denture is cleaned with the particular denture cleanser product according to its instructions, the denture is then passed through seven rinses of water to remove the residual cleansing ingredients and photographed. The lighter the red color of the denture, the greater the bleaching efficacy of that denture cleanser being tested. For cleansing efficacy (plaque removal) test the denture is stained once again for 2 minutes in 1% erythrosin solution and passed through seven rinses of water and then photographed. The lighter the red color on the denture, the greater the cleansing (plaque-removing) efficacy of that denture cleanser product.

A typical denture cleanser of this invention will remove plaque from a denture which has been worn, say, about 16 hours, to the following extent: about 85% of the plaque is removed if the denture is soaked for about 7 minutes in a warm (110°–120°F, 43°–49°C) solution of the denture cleanser (using about 4 grams of cleanser in 120 ml water); at total soaking periods of 10, 15 and 30 minutes the percentages of plaque removal are 90%, 93% and 100%, respectively. With the multicolor changes (owing to the use of two different dyes) described above, the denture wearer can obtain the degree of cleaning he desires consistent with the available soaking time. Conventional effervescent denture cleansers based on active oxygen show very much lower plaque removal.

Conventional dentures are composed of porcelain or organic plastic teeth (e.g. of acrylic resin) set into an organic plastic base (e.g. of an acrylic resin such as polymerized methyl methacrylate) which is colored pink to simulate the gums of the wearer. The plaque accumulates on the teeth and on the base as well.

As is well known in the art, certain combinations of active chlorine and nitrogen compounds (e.g. ammonium salts, urea peroxide) yield nitrogen chloride which is a toxic gas. It is of course preferable to use such ingredients and proportions that formation of significant amounts of nitrogen chloride is avoided.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

I claim:

1. A solid denture cleanser which on mixing with water effervesces and dissolves in the water to form a solution for soaking dentures, said cleanser comprising a dry stable mixture of a peroxygen compound which yields active oxygen on admixture with water and a chlorine compound which liberates hypochlorite chlorine on contact with water, said peroxygen compound being reactive with the components of said mixture in the presence of said water to liberate bubbles of gas effervesantly, said chlorine compound being present in amount sufficient to provide an amount of hypochlorite chlorine such that the atomic ratio of hypochlorite chlorine to active oxygen of said peroxygen compound is at least greater than about 1.1:1 whereby to provide at least about 100 ppm. of hypochlorite chlorine in water solution after oxygen formation has ceased and an alkaline material comprising a water-soluble anhydrous, alkaline salt which is sufficiently alkaline to give a pH of at least about 9.

2. A cleanser as in claim 1 further containing from about 0.01 to 1% of surfactant selected from the group consisting of anionic, nonionic, cationic and amphoteric surfactants capable of promoting foaming.

3. A cleanser as in claim 1 further containing at least one tabletting aid selected from the group consisting of binders, lubricants and disintegrating aids substantially inert under the conditions of use of the cleanser, the total amount of said tabletting aid being less than 50% of the total weight of cleanser composition.

4. A cleanser as in claim 5 wherein said tabletting aid is selected from the group consisting of glucose, gum acacia, gelatin, sucrose, starches, talc, magnesium stearate and polyethylene glycol having a molecular weight of from 600 to 4,000.

5. A cleanser as in claim 3 in the form of a tablet having a volume of from about 1 to 5 cc.

6. A cleanser as in claim 3 in the form of a powder the granules of which have particle sizes within the range such as to pass through a U.S. Standard 10 or 20 mesh sieve and be retained on a U.S. Standard 40 mesh sieve.

7. A cleanser as in claim 1 in which said alkaline material is present in amount to give a pH of above about 10.5.

8. A cleanser as in claim 1 in which said peroxygen compound comprises sodium perborate monohydrate, potassium monopersulfate or sodium carbonate peroxhydrate or mixtures thereof and said chlorine compound comprises sodium or potassium dichloroisocyanurate, trichloroisocyanuric acid, or mixtures thereof, and said alkaline material comprises sodium carbonate or trisodium phosphate or mixtures thereof.

9. A cleanser as in claim 1 in which said atomic ratio is at least about 2:1.

10. A cleanser as in claim 9, the proportions and nature of the ingredients thereof being such that when 3.6 grams of the composition is mixed with 120 ml of water, at the conclusion of the effervescence the pH of the resulting solution is about 10.6 to 11.5 and the active chlorine content of the resulting solution is at least 100 ppm.

11. A cleanser as in claim 10 in which said active chlorine content is up to about 1500 ppm.

12. A cleanser as in claim 11 in which said active chlorine content is above about 400 ppm.

13. A cleanser as in claim 10 in which said atomic ratio is in the range of about 2:1 to 3:1.

14. A cleanser as in claim 10 in which said atomic ratio is about 2.2:1.

15. A cleanser as in claim 13 in which said peroxygen compound is a hydrogen peroxide addition compound.

16. A cleanser as in claim 1 in which said peroxygen compound is a water-soluble monopersulfate which reacts with at least one alkaline component of said cleanser, on admixture of said cleanser with said water, to give off oxygen bubbles.

17. A cleanser as in claim 16 in which said peroxygen compound is potassium monopersulfate and said reactive alkaline component comprises trisodium phosphate.

18. Process for cleaning dentures comprises mixing water with a solid denture cleanser as defined in claim 1 and soaking said denture in said solution.

19. Process for cleaning dentures having dental plaque thereon as set forth in claim 18 in which said solution has a pH of about 10.6 to 11.5 and an active chlorine content of at least 100 ppm.

20. Process as in claim 19 in which said chlorine content is in the range of about 400 to 1500 ppm.

21. A denture cleanser as in claim 1 and comprising a first coloring agent and a second coloring agent, both of said agents being bleached by the action of said solution on standing, with said first coloring agent being bleached more rapidly, said first coloring agent being present in such concentration that its color predominates in said solution initially and for a plurality of minutes thereafter, the color of said second coloring agent thereafter becoming visible on standing for a period of less than 1 hour, owing to loss of color of said first coloring agent.

* * * * *